United States Patent [19]
Romano

[11] Patent Number: 5,729,348
[45] Date of Patent: Mar. 17, 1998

[54] FLUORESCENCE DOT AREA METER

[75] Inventor: David J. Romano, Lowell, Mass.

[73] Assignee: Agfa Division, Bayer Corporation, Wilmington, Mass.

[21] Appl. No.: 701,028

[22] Filed: Aug. 21, 1996

[51] Int. Cl.$^6$ .................................................. G01N 2/64
[52] U.S. Cl. .................. 356/417; 350/458.1; 350/459.1; 356/379
[58] Field of Search .................................. 356/417, 379; 250/458.1, 459.1

[56] References Cited

U.S. PATENT DOCUMENTS

| | | | |
|---|---|---|---|
| 4,339,525 | 7/1982 | Bratt et al. | 430/271 |
| 4,516,856 | 5/1985 | Popelka | 356/417 X |
| 5,099,131 | 3/1992 | Brownrigg et al. | 250/458.1 |
| 5,578,818 | 11/1996 | Kain et al. | 250/458.1 X |

*Primary Examiner*—Vincent P. McGraw
*Attorney, Agent, or Firm*—John A. Merecki

[57] ABSTRACT

A fluorescence dot area meter for accurately measuring halftone dot area on a printing plate having an emulsion containing one or more fluorescent compounds. The fluorescent dot area meter generally includes an illumination source for providing light having a first range of wavelengths, a system for exposing the printing plate to this light to cause the printing plate to emit light (fluoresce) within a second, higher range of wavelengths, and a system for determining halftone dot area based on a measurement of the light emitted by the printing plate.

24 Claims, 4 Drawing Sheets

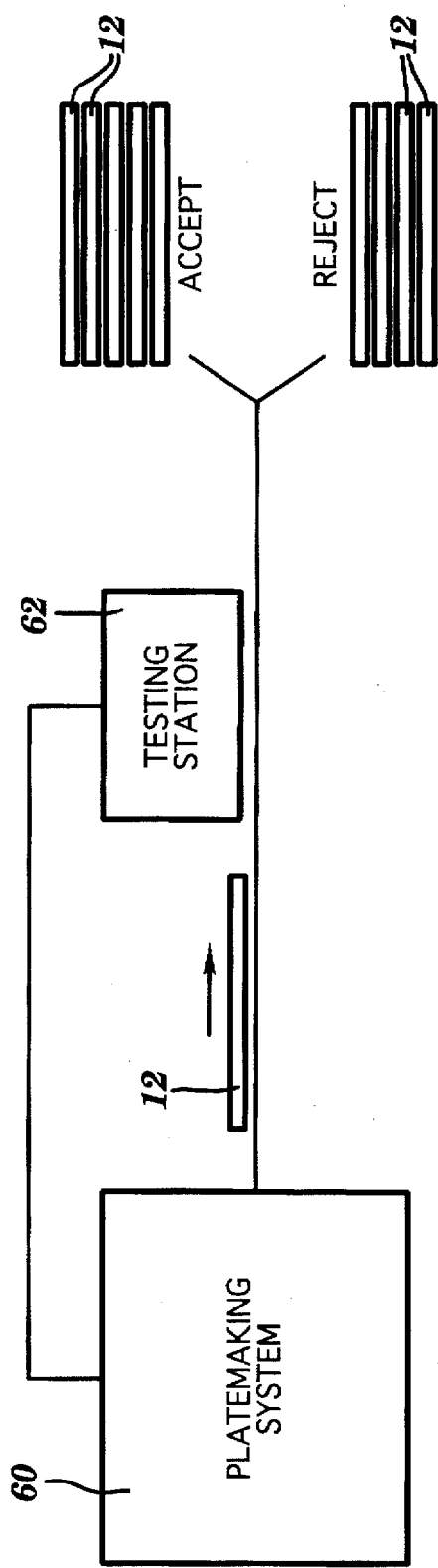

FLUORESCENCE DOT AREA METER

FIELD OF THE INVENTION

The present invention provides a method and apparatus for accurately measuring halftone dot area on a printing plate having an emulsion containing one or more fluorescent compounds.

BACKGROUND OF THE INVENTION

Reflection densitometers provide an accurate measurement of halftone dot area on prints produced by an output device such as a printing press or the like. Unfortunately, the reflection densitometer has been proven to be unreliable for measuring halftone dot area on printing plates. This is due in part to the reflective directionality of the grain of the printing plate. Regardless of the cause, a reflection densitometer will typically provide contradictory readings if rotated even slightly over an area of a printing plate being measured.

SUMMARY OF THE INVENTION

The present invention provides a fluorescence dot area meter for accurately measuring halftone dot area on a printing plate. The fluorescent dot area meter generally includes an illumination source for providing light having a first range of wavelengths, a system for exposing the printing plate to this light to cause the printing plate to emit light (fluoresce) within a higher, second range of wavelengths, and a system for determining halftone dot area based on a measurement of the light emitted by the printing plate.

BRIEF DESCRIPTION OF THE DRAWINGS

The features of the present invention will best be understood from a detailed description of the invention and a preferred embodiment thereof selected for the purposes of illustration and shown in the accompanying drawings in which:

FIG. 5 illustrates a platemaking system incorporating a printing plate testing station, wherein the testing station includes the fluorescence dot area meter of the present invention; and FIG. 6 is a example of a look-up table for use in the testing station of FIG. 5.

DETAILED DESCRIPTION OF THE INVENTION

Figure 1:
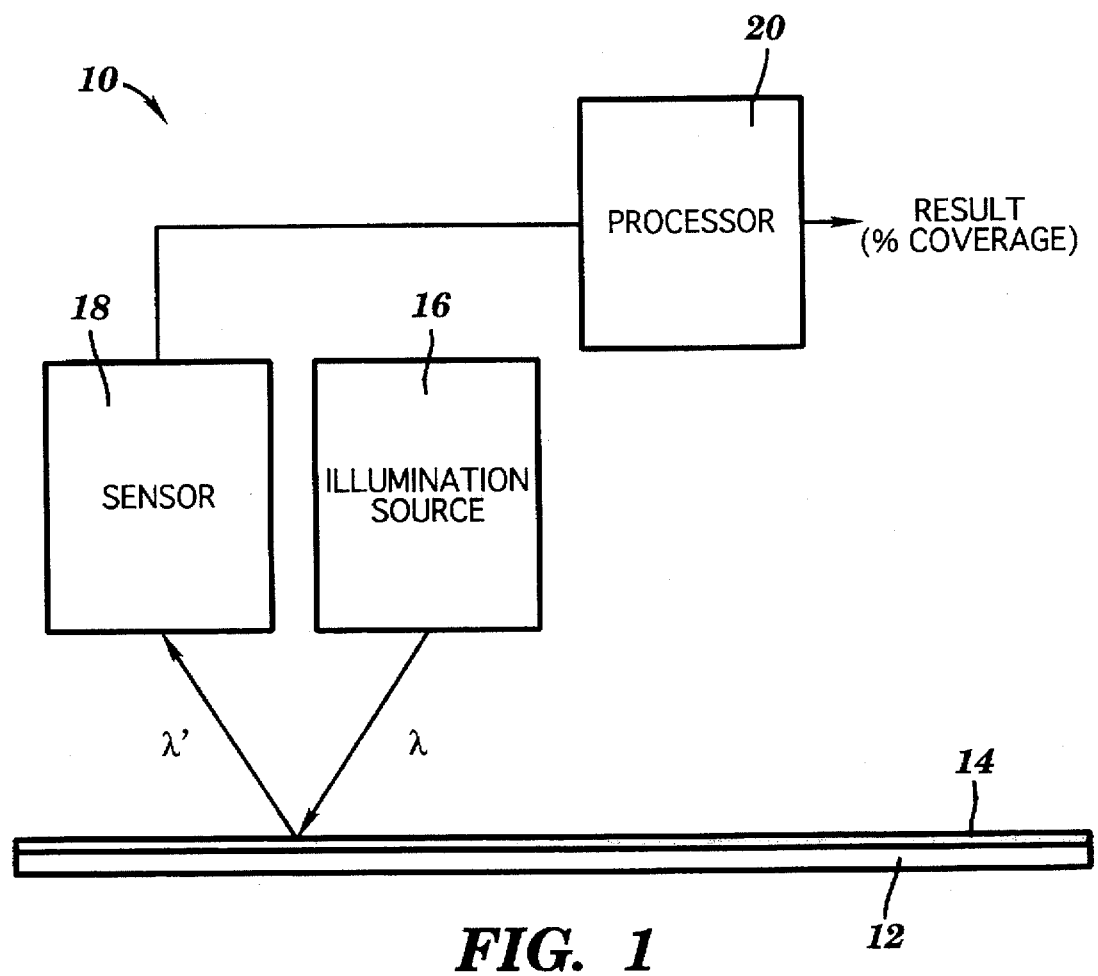
FIG. 1 illustrates a general block diagram of a fluorescence dot area meter in accordance with the present invention.

The objects, features, and advantages of the present invention are illustrated in detail in the accompanying drawings, wherein like reference numerals refer to like elements throughout the drawings.

A general block diagram of a fluorescence dot area meter 10 in accordance with the present invention is illustrated in FIG. 1. The fluorescence dot area meter 10 is used to provide halftone dot area measurements on a printing plate 12 having a surface emulsion 14 including one or more fluorescent compounds. As known in the art, the areas of emulsion 14 remaining on the surface of the printing plate 12 after the plate has been recorded and developed correspond to recorded halftone dots.

The fluorescence dot area meter 10 includes an illumination source 16. The illumination source 16 provides light $\lambda$, having a first range of wavelengths with sufficient energy to cause particular molecules in the emulsion 14 remaining on the surface of the printing plate 12 to become excited enough to emit light $\lambda'$ within a second, higher range of wavelengths (i.e., to fluoresce). This is illustrated in FIG. 1. Specifically, the printing plate 12 is exposed to the light $\lambda$, emitted by the illumination source 16, causing the emulsion 14 remaining on the printing plate 12 to reemit light $\lambda'$ within a second, higher range of wavelengths.

The light $\lambda'$ reemitted by a section of the printing plate 12 is isolated and detected by a sensor 18. The output of the sensor 18 is provided to a processor 20 which calculates the percentage of the area within the section of the printing plate 12 that is covered by halftone dots (% coverage). Generally, each section of the printing plate 12 to be measured corresponds to a predetermined halftone test pattern, such as a 50% halftone comprising 8×8 dot pixels. If the area measurements output by the processor 20 are not satisfactory, various platemaking variables, such as exposure, focus and pulse width modulation, can be adjusted as required to optimize the characteristics (e.g., size, shape) of the halftone dots recorded on the printing plate 12.

The fluorescence dot area meter 10 is designed to be used with printing plates 12 having a surface emulsion 14 containing one or more fluorescent compounds. For example, the fluorescence dot area meter 10 of the present invention can be used to determine halftone dot area measurements on the aluminum N90™ printing plate manufactured by the Agfa Division of Bayer Corporation. Specifically, yellow light in the region of about 540–640 nm, peaking at 570 nm, is reemitted by the recorded dots on the aluminum N90™ printing plate when the plate is exposed to blue light in the region of about 450–500 nm. The reemitted yellow light can be viewed and measured by filtering out the blue light reflected by the unexposed sections of the plate.

The fluorescence dot area meter 10 calculates dot area using a variation of the well known Yule-Neilsen equation (EQU. 1). As known in the art, the Yule-Neilsen equation is commonly used to determine the dot area on prints using measurements provided by a reflection densitometer. The Yule-Neilsen equation is presented in detail in an article entitled "The Penetration of Light into Paper and its Effects on Halftone Reproduction" (Yule and Neilsen, TAGA Proceedings, 1951, pp. 65–76), incorporated herein by reference.

$$\% = \frac{1 - 10^{\frac{-(t-p)}{N}}}{1 - 10^{\frac{-(s-p)}{N}}} \times 100 \qquad \text{(EQU. 1)}$$

Where:
  %=Percent of print area covered by halftone dots
  t=Density of the halftone tint area
  p=Density of the paper or background area
  s=Density of the solid or 100% covered area
  N=N-factor used to correct for optical effects Since the fluorescence dot area meter 10 measures the amount of reemitted light, rather than the absence of light (i.e., density), the Yule-Neilsen equation is simplified:

$$\% = \frac{(t-p)^N}{(s-p)^N} \times 100 \qquad \text{(EQU. 2)}$$

The purpose of the N-factor in EQU. 1 is to account for light which penetrates the translucent surface of paper, where it becomes trapped under, and is absorbed by, the ink of the halftone dots. This effectively creates a shadow around the dots. Since a reflection densitometer only measures integral densities, it cannot differentiate between a halftone dot and the optically created shadows. This effect, which is commonly referred to as "optical dot gain", increases the measured dot area. The N-factor in EQU. 1 lowers the measured dot areas to better approximate the real geometric are of the halftone dots.

The fluorescence dot area meter 10 measures halftone dots on the opaque surface of the printing plate 12 by measuring brightness rather than density. As a consequence, the effect of optical dot gain is reversed and becomes "optical dot sharpening." In this case, as presented in EQU. 2, the N-factor is used to increase the dot areas in order to correct for brightness losses due to optical effects and other factors.

The N-factor is determined by first measuring a sample of halftone dots on a printing plate using an image analysis system. This establishes the actual geometric area of the dots. This measurement is then compared to the output of the fluorescence dot area meter 10 for the same sample of halftone dots. The N-factor is adjusted in EQU. 2 until the dot area measurement provided by the meter 10 matches the actual geometric area of the dots as closely as possible.

Figure 2:
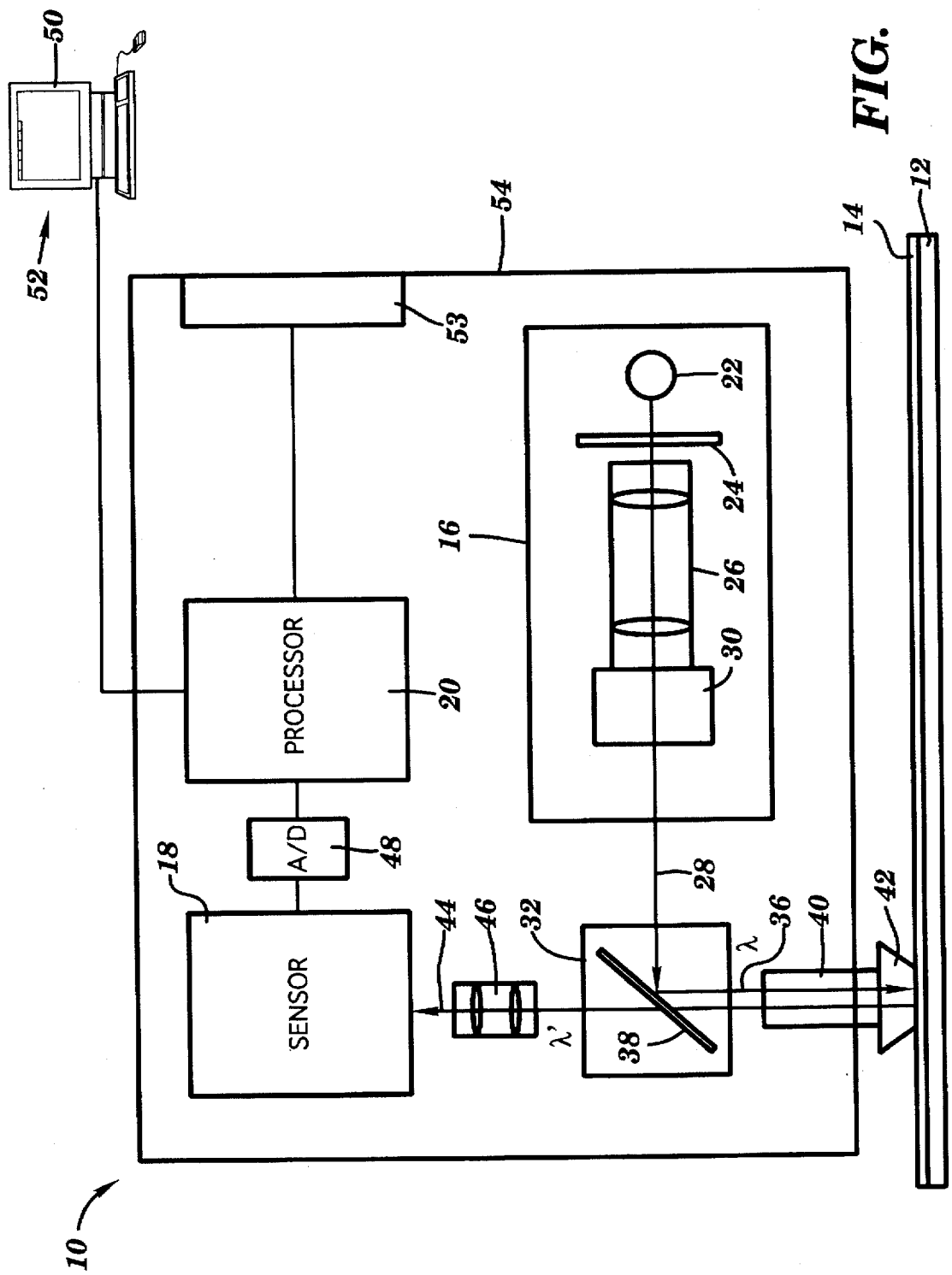
FIG. 2 illustrates in detail a first embodiment of the fluorescence dot area meter.

The fluorescence dot area meter 10 of the present invention is illustrated in greater detail in FIG. 2. As shown, the illumination source 16 comprises a lamp 22, a layer of heat absorbing glass 24, and a collimator 26 for focusing the output of the lamp 22 into a light beam 28. Preferably, a low wattage, high intensity lamp 22 is used, such as a 50–100 W halogen lamp, to prevent excessive heat build up within the meter 10, and to avoid heating or quenching the surface of the printing plate 12. The layer of heat absorbing glass 24 is used to attenuate the heat produced by the lamp 22.

The illumination source 16 further includes an adjustable field aperture 30. The adjustable field aperture 30 allows a user to adjust the area of the printing plate to be tested using the fluorescence dot area meter 10. Preferably, the field aperture 30 can be adjusted from 1 mm to 5 mm using a lever, knob, or other device accessible from the outside of the meter 10.

Figure 3:
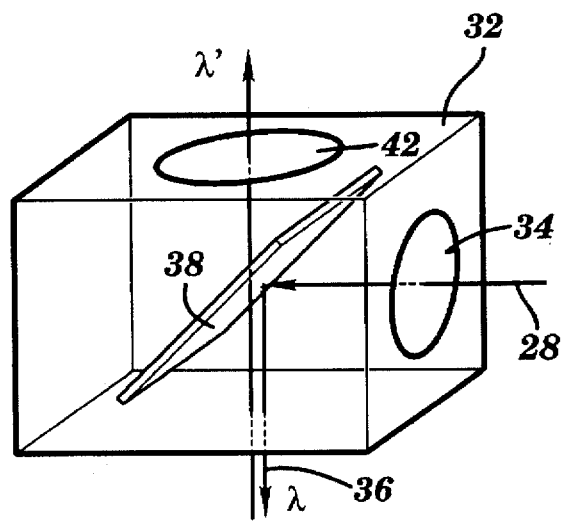
FIG. 3 shows a filter cube assembly for use in the fluorescence dot area meter of the present invention.

The light beam 28 produced by the illumination source 16 is directed into an interchangeable filter cube assembly 32. The filter cube assembly 32 is illustrated in greater detail in FIG. 3. The filter cube assembly 32 includes a first optical filter 34 for filtering the light beam 28 to produce a light beam 36 having a first range of wavelengths. In the case of the above-described N90™ plate manufactured by the Agfa Division of Bayer Corporation, for example, the first optical filter 34 can be a short pass filter having an upper cutoff of approximately 500 nm, or a bandpass filter having a range of about 450–500 nm.

After being filtered by the first optical filter 34, the light beam 36 is perpendicularly redirected toward the printing plate 12 by a dichroic beam splitter mirror 38. As known in the art, a dichroic beam splitter mirror 38 is designed to reflect light within a first range of wavelengths, and to transmit light within a second, different range of wavelengths. The redirected light beam 36 is subsequently directed against the printing plate 12 through an objective lens assembly 40. A lens shield 42 is coupled to the distal end of the objective lens assembly 40 to eliminate outside light contamination.

The light reemitted by the emulsion layer 14 of the printing plate 12 passes through the objective lens assembly 40, through the dichroic beam splitter mirror 38, and through a second optical filter 42. The second optical filter 42 serves to selectively pass only that light λ' having wavelengths corresponding to the light reemitted by the emulsion layer 14. Other light, such as the light λ reflected by the non-emulsion areas of the printing plate, are blocked by the second optical filter 42. For the N90™ plate manufactured by the Agfa Division of Bayer Corporation, for example, the second optical filter 42 can be a long pass filter having an lower cutoff of approximately 540 nm, or a bandpass filter having a range of about 540–640 nm.

The output of the second optical filter 42 is focused into a light beam 44 by a focusing lens assembly 46, and directed into the sensor 18. Preferably, the sensor 18 comprises a photomultiplier tube (PMT) sensor of a type known in the art. Other types of sensors, such as a silicon diode, a CCD sensor, or the like can also be used without departing from the scope of the present invention. The output of the sensor 18 is passed through an analog-to-digital converter 48 to the processor 20, which calculates dot area on the printing plate 12 in accordance with EQU. 2. The results of the dot area calculation are output to a user via the display 50 of a workstation 52, or on an LCD panel/user interface 53 on the meter 10.

Figure 4:
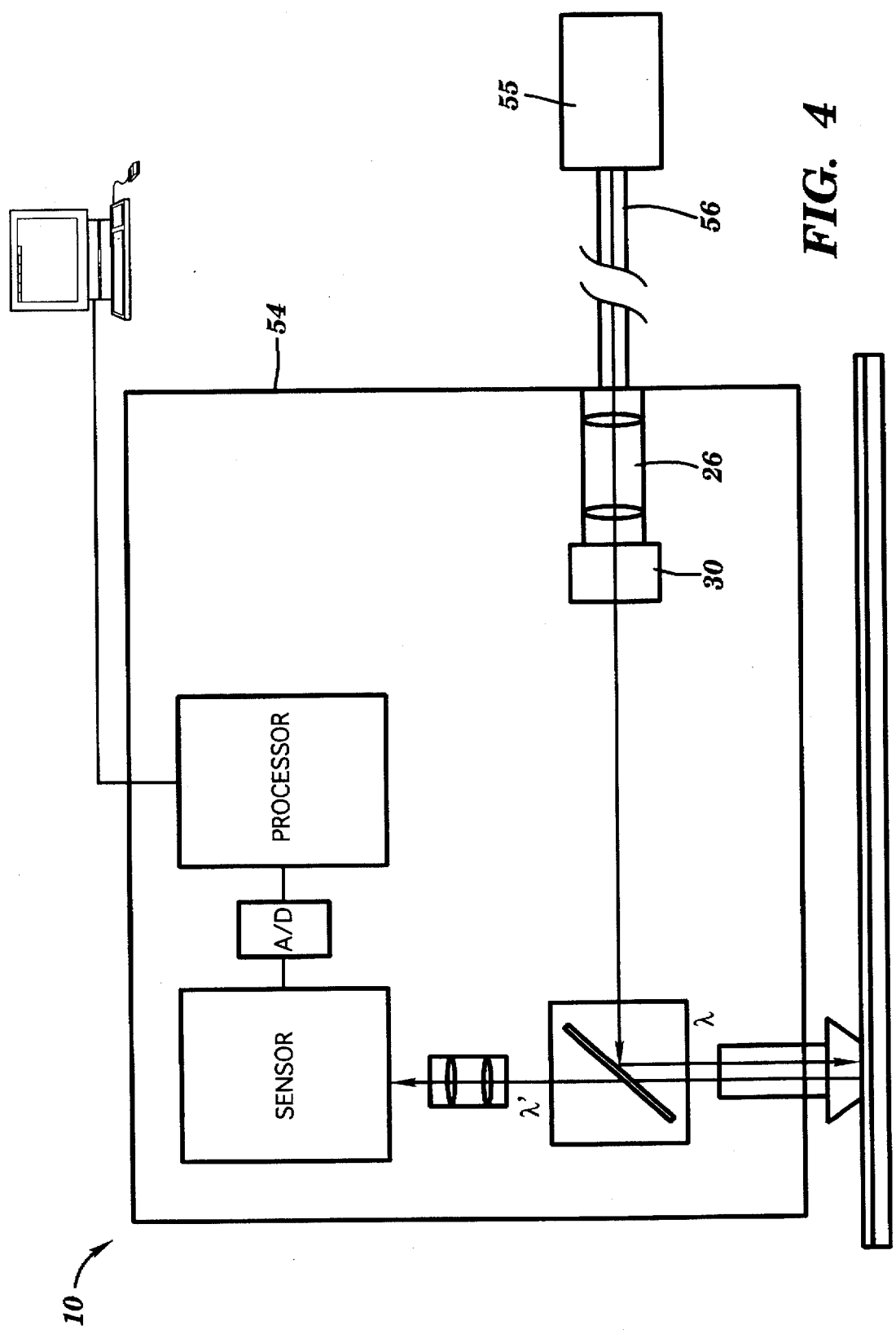
FIG. 4 illustrates a general block diagram of a fluorescence dot area meter utilizing an external illumination source.

As illustrated in FIG. 2, the illumination source 16 (and associated power source) are preferably enclosed within the main body 54 of the fluorescence dot area meter 10. To increase the portability of the meter 10, however, an external illumination source 55 and/or associated power source can be used. Specifically, as shown in FIG. 4, a fiber optic cable 56 or the like can be used to direct the output of the externally disposed illumination source 55 into the fluorescence dot area meter 10 through the collimator 26 and adjustable field aperture 30. In this manner, the weight of the fluorescence dot area meter 10 can be greatly reduced, allowing a user to easily move the meter 10 by hand over the surface of the printing plate 12.

The dot area results output by the fluorescence dot area meter 10 are typically used to optimize the performance of a platemaking system. Generally, an operator manually adjusts various platemaking variables in response to the output of the fluorescence dot area meter 10. However, the fluorescence dot area meter 10 can be incorporated into a feedback loop in which the platemaking variables are automatically adjusted according to the type of printing plate 12 being used to optimize the performance of a platemaking system. Such a system is illustrated in FIG. 5.

As each printing plate 12 exits the platemaking system 60, it passes through a testing station 62 including a fluorescence dot area meter 10. The fluorescence dot area meter 10 analyzes at least one predetermined test pattern recorded on a portion of the printing plate 12. The output of the fluorescence dot area meter 10 is subsequently compared to a predetermined "optimum" dot area measurement, and the printing plate 12 is either accepted or rejected according to the result of this comparison. If the printing plate 12 is rejected, the testing station 62 selectively outputs a set of updated platemaking variables, depending upon the output of the fluorescence dot area meter 10 and the type of printing plate 12, to adjust the output quality of the platemaking system 60.

The testing station 62 stores a set of information specific to each type of printing plate 12 output by the platemaking system 60 in a look-up table 64. An example of a look-up table 64 for a printing plate 12 of type "PLATE A" is illustrated in FIG. 6. In this example, the fluorescence dot area meter 10 of the present invention analyzes a 50% test pattern recorded on a portion of the printing plate 12. The output of the fluorescence dot area meter 10 is compared to the % coverage data 66 stored in the look-up table 64. If the output of the meter 10 falls within an acceptable range (49%–51% in this example) the printing plate is accepted. If the output of the meter 10 falls outside of the acceptable range (e.g., ≦48%, ≧52%), the printing plate is rejected. In this case, a set of predetermined platemaking variables 68 are provided to the platemaking system 60 to bring the output quality of the system within the acceptable range.

As described above, the fluorescence dot area meter 10 of the present invention uses the fluorescence of the emulsion 14 on a printing plate 12 to accurately measure halftone dot area. Although the meter 10 can be used with many types of currently available printing plates, such as the aluminum N90™ printing plate manufactured by the Agfa Division of Bayer Corporation, not all printing plates are capable of fluorescence. However, by adding a suitable fluorescent compound to the emulsion of a printing plate during the manufacture of the plate, most, if not all, printing plates can be used with the present invention.

The foregoing description of the present invention has been presented for purposes of illustration and description. It is not intended to be exhaustive or to limit the invention to the precise form disclosed, and many modifications and variations are possible in light of the above teaching. Such modifications and variations that may be apparent to a person skilled in the art are intended to be included within the scope of this invention as defined by the accompanying claims.

I claim:

1. An apparatus for measuring halftone dot area on a printing plate, comprising:
   an illumination source for illuminating said printing plate;
   a sensor for detecting light reemitted by said printing plate; and
   processor means, coupled to said sensor, for determining halftone dot area based on the light reemitted by said printing plate.

2. The apparatus for measuring halftone dot area according to claim 1, wherein said illumination source provides light having a first range of wavelengths.

3. The apparatus for measuring halftone dot area according to claim 2, wherein said printing plate reemits light within a second, higher range of wavelengths.

4. The apparatus for measuring halftone dot area according to claim 3, wherein said illumination source includes a light source and first filter means for filtering an output of said light source to provide light having said first range of wavelengths.

5. The apparatus for measuring halftone dot area according to claim 4, wherein said sensor includes second filter means for isolating the light reemitted by said printing plate.

6. The apparatus for measuring halftone dot area according to claim 5, wherein said first and second filter means are disposed within a filter cube.

7. The apparatus for measuring halftone dot area according to claim 6, wherein said filter cube is interchangeable based on characteristics of the printing plate on which halftone dot area measurements are being determined.

8. The apparatus for measuring halftone dot area according to claim 6, wherein said filter cube further includes a dichroic beam splitter mirror.

9. The apparatus for measuring dot area according to claim 8, wherein said dichroic beam splitter mirror reflects the light having said first range of wavelengths, and transmits the light reemitted by said printing plate.

10. The apparatus for measuring halftone dot area according to claim 1, wherein said printing plate includes an emulsion containing at least one fluorescent compound.

11. The apparatus for measuring halftone dot area according to claim 3, wherein said printing plate includes an emulsion containing at least one fluorescent compound, and wherein said emulsion reemits light having said second, higher range of wavelengths.

12. The apparatus for measuring halftone dot area according to claim 1, wherein said illumination source includes an adjustable field aperture for setting a measurement area on said printing plate.

13. The apparatus for measuring halftone dot area according to claim 1, wherein said illumination source includes a light source, means for attenuating the heat produced by said light source, and a collimating assembly for focusing an output of said light source into a light beam.

14. The apparatus for measuring halftone dot area according to claim 1, further including means for displaying the halftone dot area measurement output by said processor means.

15. A measurement apparatus comprising:
   means for measuring a fluorescent characteristic of a printing plate; and
   means for determining a halftone dot area on said printing plate based on the fluorescent characteristic of said printing plate.

16. The measurement apparatus according to claim 15, wherein said printing plate includes an emulsion containing at least one fluorescent compound.

17. The measurement apparatus according to claim 16, wherein said measuring means further includes an illumination source for illuminating said printing plate with light having a first range of wavelengths, and a sensor for detecting light reemitted by the emulsion of said printing plate at a second, higher range of wavelengths, and wherein said determining means further includes a processor means, coupled to said sensor, for determining halftone dot area based on the light reemitted by the emulsion of said printing plate.

18. A platemaking system, comprising:
   a platemaker for producing printing plates;
   a test station for analyzing a predetermined test pattern on a printing plate produced by said platemaker, said test station including means for measuring halftone dot area on said printing plate based on a fluorescent characteristic of said printing plate; and
   means for providing said platemaker with an updated set of platemaking variables based on the halftone dot area measurement provided by said measuring means.

19. The platemaking system according to claim 18, wherein said test station further includes:
   means for selectively accepting or rejecting a printing plate produced by said platemaker based on the halftone dot area measurement provided by said measuring means.

20. The platemaking system according to claim 18, wherein said printing plate includes an emulsion containing at least one fluorescent compound.

21. The platemaking system according to claim 20, wherein said measuring means includes:
   an illumination source for illuminating said printing plate with light having a first range of wavelengths, a sensor for detecting light reemitted by the emulsion of said printing plate at a second, higher range of wavelengths, and processor means, coupled to said sensor, for determining halftone dot area based on the light reemitted by the emulsion of said printing plate.

22. A method for measuring halftone dot area on a printing plate, comprising the steps 4:

illuminating said printing plate with light having a first range of wavelengths;

detecting light within a second, higher range of wavelengths reemitted by said printing plate; and determining halftone dot area based on the light reemitted by said printing plate.

23. The method for measuring halftone dot area according to claim 22, further including the steps of:

providing said printing plate with an emulsion containing at least one fluorescent compound.

24. A method for measuring halftone dot area on a printing plate having an emulsion containing at least one fluorescent compound, comprising the steps of:

exposing said printing plate to light; and determining halftone dot area on said printing plate by measuring light reemitted by the emulsion of said printing plate.

* * * * *